(12) United States Patent
Eismann et al.

(10) Patent No.: US 11,025,721 B2
(45) Date of Patent: *Jun. 1, 2021

(54) DATA TRANSFER BETWEEN AN X-RAY DETECTOR AND AN ARITHMETIC UNIT VIA A NETWORK PROTOCOL

(71) Applicant: Siemens Healthcare GmbH, Erlangen (DE)

(72) Inventors: Alfons Eismann, Pinzberg (DE); Thorsten Ergler, Erlangen (DE); Taras Pryymak, Fuerth (DE); Bodo Reitz, Forchheim (DE); Alexander Graf, Forchheim (DE); Edmund Goetz, Effeltrich (DE); Stefan Hartmann, Eggolsheim (DE); Thomas Hilderscheid, Altdorf (DE); Shameem Kabir Chaudhury, Erlangen (DE); Kurt Stadlthanner, Fuerth (DE); Michael Hosemann, Erlangen (DE)

(73) Assignee: Siemens Healthcare GMBH, Erlangen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/717,188

(22) Filed: Dec. 17, 2019

(65) Prior Publication Data

US 2020/0128079 A1    Apr. 23, 2020

Related U.S. Application Data

(63) Continuation of application No. 15/728,644, filed on Oct. 10, 2017, now Pat. No. 10,547,685.

(30) Foreign Application Priority Data

Oct. 27, 2016 (DE) .......................... 102016221221.4

(51) Int. Cl.
*H04L 29/08* (2006.01)
*H04J 3/06* (2006.01)
(Continued)

(52) U.S. Cl.
CPC ................ *H04L 67/12* (2013.01); *A61B 6/03* (2013.01); *A61B 6/032* (2013.01); *A61B 6/42* (2013.01);
(Continued)

(58) Field of Classification Search
CPC ......... H04L 67/12; G01T 1/2964; G01T 1/20; G01T 7/00; A61B 6/563; A61B 6/42;
(Continued)

(56) References Cited

U.S. PATENT DOCUMENTS

2003/0068006 A1   4/2003   Beyerlein et al.
2003/0185338 A1   10/2003  Dafni et al.
(Continued)

FOREIGN PATENT DOCUMENTS

CN   103701811 A   4/2014
CN   104509216 A   4/2015
(Continued)

OTHER PUBLICATIONS

Chinese Office Action dated Jun. 1, 2020 issued in Chinese Patent Application No. 201711024048.6. English translation has been provided.

(Continued)

*Primary Examiner* — Moo Jeong
(74) *Attorney, Agent, or Firm* — Harness, Dickey & Pierce, P.L.C.

(57) ABSTRACT

A detector apparatus for use as part of a data network includes a plurality of x-ray detectors, each of the plurality of x-ray detectors including a network-capable network interface, and a switch or router, connected to each of the (Continued)

network-capable network interfaces of the plurality of x-ray detectors, each of the plurality of x-ray detectors including a distinct IP address such that the data network is adjustable to take a change in a number of the plurality of x-ray detectors into account. The plurality of x-ray detectors are configured to detect x-rays generated from a single x-ray source.

20 Claims, 3 Drawing Sheets

(51) Int. Cl.
<table>
<tr><td>G01T 7/00</td><td>(2006.01)</td></tr>
<tr><td>G01T 1/29</td><td>(2006.01)</td></tr>
<tr><td>G01T 1/20</td><td>(2006.01)</td></tr>
<tr><td>A61B 6/03</td><td>(2006.01)</td></tr>
<tr><td>A61B 6/00</td><td>(2006.01)</td></tr>
</table>

(52) U.S. Cl.
CPC ........... *A61B 6/4266* (2013.01); *A61B 6/563* (2013.01); *G01T 1/20* (2013.01); *G01T 1/2964* (2013.01); *H04J 3/0661* (2013.01); *H04J 3/0676* (2013.01); *G01T 7/00* (2013.01); *H04J 3/0667* (2013.01)

(58) Field of Classification Search
CPC ......... A61B 6/4266; A61B 6/032; A61B 6/03; H04J 3/0661; H04J 3/0676; H04J 3/0667
See application file for complete search history.

(56) References Cited

U.S. PATENT DOCUMENTS

<table>
<tr><td>2005/0169263 A1</td><td>8/2005</td><td>Grottel et al.</td></tr>
<tr><td>2007/0146130 A1</td><td>6/2007</td><td>Hannemann et al.</td></tr>
<tr><td>2008/0049901 A1</td><td>2/2008</td><td>Tamakoshi</td></tr>
<tr><td>2010/0098316 A1</td><td>4/2010</td><td>Papaioannou</td></tr>
<tr><td>2011/0268247 A1</td><td>11/2011</td><td>Shedlock et al.</td></tr>
<tr><td>2013/0188629 A1</td><td>7/2013</td><td>Lemaire et al.</td></tr>
<tr><td>2014/0046617 A1</td><td>2/2014</td><td>Campagna</td></tr>
<tr><td>2015/0208489 A1</td><td>7/2015</td><td>Dijk et al.</td></tr>
<tr><td>2016/0015341 A1*</td><td>1/2016</td><td>Lee ............................ G01T 1/17 250/395</td></tr>
<tr><td>2016/0143609 A1*</td><td>5/2016</td><td>Park ....................... A61B 6/547 378/98.2</td></tr>
<tr><td>2016/0217596 A1*</td><td>7/2016</td><td>Koehler ................ G06T 11/006</td></tr>
</table>

FOREIGN PATENT DOCUMENTS

<table>
<tr><td>DE</td><td>10150048 A1</td><td>5/2003</td></tr>
<tr><td>DE</td><td>10354494 A1</td><td>6/2005</td></tr>
<tr><td>DE</td><td>102012213948 A1</td><td>2/2014</td></tr>
<tr><td>DE</td><td>102015211912 A1</td><td>12/2016</td></tr>
</table>

OTHER PUBLICATIONS

Chinese Office Action dated Sep. 28, 2020 issued in corresponding Chinese Patent Application No. 201711024048.6. English translation has been provided.

* cited by examiner

DATA TRANSFER BETWEEN AN X-RAY DETECTOR AND AN ARITHMETIC UNIT VIA A NETWORK PROTOCOL

PRIORITY STATEMENT

The present application is a continuation of U.S. application Ser. No. 15/728,644, filed on Oct. 10, 2017, which claims priority under 35 U.S.C. § 119 to German patent application number DE 102016221221.4 filed Oct. 27, 2016, the entire contents of each of which are hereby incorporated herein by reference.

FIELD

At least one embodiment of the invention generally relates to a detector apparatus, a medical device and/or a method for operating a detector apparatus, wherein the data is transferred between an x-ray detector and an arithmetic unit via a network protocol.

BACKGROUND

In x-ray imaging, for instance in computed tomography, angiography or radiography, counting direct-conversion x-ray detectors or integrated indirect-conversion x-ray detectors can be used.

The x-ray radiation or the photons can be converted in direct-conversion x-ray detectors by a suitable converter material into electric pulses. CdTe, CZT, CdZnTeSe, CdTeSe, CdMnTe, InP, $TlBr_2$, $HgI_2$, GaAs or others can be used as the converter material, for example. The electric pulses are evaluated by an evaluating electronic system, for example an integrated circuit (Application Specific Integrated Circuit, ASIC). In counting x-ray detectors, incident x-ray radiation is measured by counting the electric pulses which are triggered by the absorption of x-ray photons in the converter material. The level of the electric pulse is generally proportional to the energy of the absorbed x-ray photon. By this means, spectral information can be extracted by comparing the level of the electric pulse with a threshold value.

The x-ray radiation or the photons can be converted in indirect-conversion x-ray detectors by a suitable converter material into light and via photodiodes into electric pulses. Scintillators, for instance GOS ($Gd_2O_2S$), CsJ, YGO or LuTAG, are frequently used as converter material. Scintillators are used particularly in medical x-ray imaging in the energy range up to 1 MeV. What are known as indirect-conversion x-ray detectors, known as scintillator detectors, are typically used, in which the conversion of the x-ray or gamma radiation into electric signals takes place in two stages. In a first stage, the x-ray or gamma quanta are absorbed in a scintillator element and converted into optically visible light; this effect is referred to as luminescence. The light excited by luminescence is then converted in a second stage by a first photodiode, which is optically coupled to the scintillator element, into an electric signal, read out by way of an evaluation or read-out electronics system and then forwarded to an arithmetic unit.

In a detector apparatus for computed tomography systems, data from many x-ray detectors is routed to a central data interface. The data is forwarded from this data interface via a slip ring transmission system to an arithmetic unit. For instance, the data can be retrieved from the individual x-ray detectors via a controller, stored in an intermediate unit, sorted and then sent to the arithmetic unit.

SUMMARY

The inventors have discovered that an underlying problem is that the intensity of the x-ray radiation can be measured in a computed tomography system during the recording in the very many pixels of the detector apparatus. The detector is made up of many, typically 30-50, x-ray detectors. The measurement time typically amounts to between 100 μs and 500 μs. The individual x-ray detectors of the detector apparatus must measure the data in synchrony with one another and output the same to a clock generator.

In at least one embodiment of the invention, a detector apparatus, a medical device and/or a method for operating a detector apparatus are disclosed, which permit the transmission of data between an x-ray detector and an arithmetic unit via a network protocol.

At least one embodiment of the invention is directed to a detector apparatus; at least one embodiment of the invention is directed to a medical device; and at least one embodiment of the invention is directed to a method for operating a detector apparatus.

At least one embodiment of the invention relates to a detector apparatus including at least one x-ray detector, which has a network-capable network unit, and a switching unit connected to the network unit of the x-ray detector.

At least one embodiment of the invention further relates to a medical device including an embodiment of the detector apparatus, a transfer unit and an arithmetic unit. The arithmetic unit can have a clock or a reference clock for synchronizing the time receiver. The arithmetic unit has at least one network interface, preferably a number of network interfaces. In the arithmetic unit the data can be used to reconstruct two or three-dimensional images.

At least one embodiment of the invention further relates to a method for operating a detector apparatus comprising detecting x-ray radiation via an x-ray detector and in the process detecting data, and of transferring data from the network unit to the switching unit via a network protocol. The detection can comprise reading out data. Advantageously the integration of the network into the detector apparatus or the communication link toward the switching unit, transfer unit or arithmetic unit can be simplified or made quicker. Advantageously in troubleshooting available data network tools can be accessed.

BRIEF DESCRIPTION OF THE DRAWINGS

Example embodiments of the invention will now be described in more detail, making reference to the drawings, in which.

DETAILED DESCRIPTION OF THE EXAMPLE EMBODIMENTS

Figure 1:
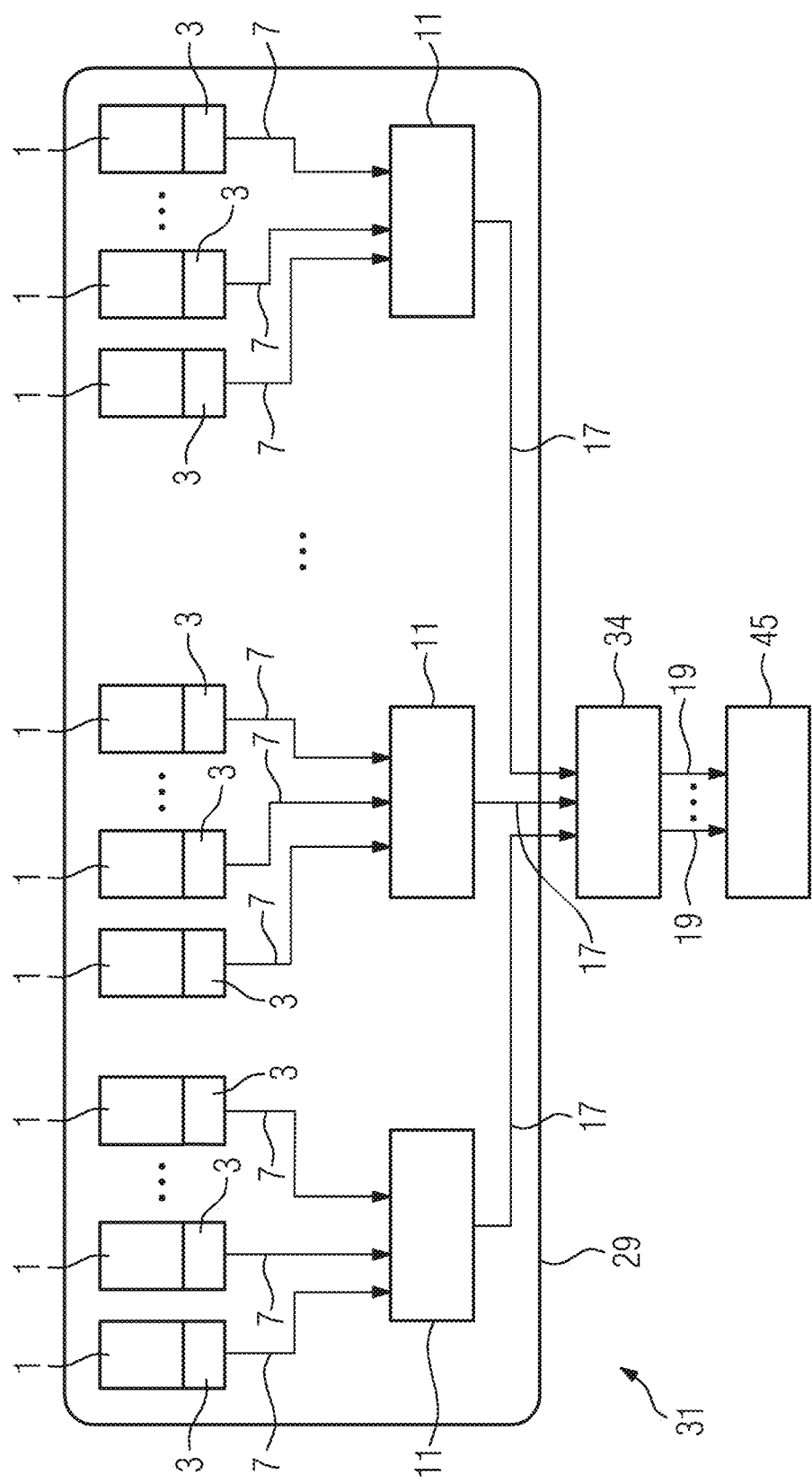
FIG. 1 shows a schematic representation of a concept of an inventive computed tomography system according to a first embodiment having an inventive detector apparatus according to a first embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a detector apparatus including at least one x-ray detector, which has a network-capable network unit, and a switching unit connected to the network unit of the x-ray detector.

In at least one embodiment, the detector apparatus includes at least one x-ray detector. The at least one x-ray detector has at least one detector element or a pixel. The x-ray detector may be a detector module. The x-ray detector may have a converter unit and an evaluation unit. The converter unit can have a direct-conversion or indirect-conversion converter material. The x-ray detector can have a buffer store. Advantageously a central buffer store can be avoided in the detector apparatus. The x-ray detector can have a buffer store.

The network unit can have a network interface. The network unit can permit access to a computer network via the network interface. The network unit is network-capable. The network unit can be connected to a number of network components which are independent of one another. The connection or communication can be established via a network protocol. The network unit can be a network component. The network interface can comprise a variant of the Ethernet standard, a BNC connector or a connector for a fiber-optic cable for instance. The network unit can be embodied to transfer data via an Internet protocol. The switching unit can be a network component. The switching unit can be a router or a switch. The switching unit has a number of network interfaces. Data losses can be compensated for by what is known as retransmit, for instance with the use of the TCP/IP protocol. A synchronous network, for instance ATM, SDH or Sonet, or an asynchronous network, for instance Ethernet, can be used.

The inventors have identified that a data transfer, which is internal and external to a detector apparatus, based on network protocols, for instance TCP/IP and Ethernet, can be used. Therefore commercially available components such as routers or switches can be used instead of self-developed data transfer links. Each x-ray detector has an interface which is available cost-effectively, TCP/IP for instance.

Advantageously, cost-effective communication hardware which is available on the market can be used for instance to transfer data from the x-ray detector toward a transfer unit further to the arithmetic unit outside of the detector apparatus. The communication can take place in just one direction for instance, known as simplex. The data can flow alternately in both directions, known as half duplex. The data can flow simultaneously in both directions, known as full duplex. With synchronous data transfer the communication can be synchronized by way of a clock signal. Alternatively an asynchronous data transfer can be used. A distinct IP address can be assigned to the x-ray detector for instance.

A distinct network, for instance a data network, can be installed in the computed tomography system. The x-ray detector can be embedded in this, for instance with a distinct IP address. A change in the number of x-ray detectors in a detector apparatus can advantageously be taken into account by adjusting the available network, instead of a new development of the overall electronics system of the detector apparatus.

The cabling work and the susceptibility to error can advantageously be reduced. Advantageously the integration of the network into the detector apparatus or the communication link toward the arithmetic unit can be simplified or made quicker. Advantageously in troubleshooting available data network tools can be accessed.

According to one embodiment of the invention, a network protocol is used for communication between the network unit and the switching unit. The network protocol is a communication protocol for exchanging data between the x-ray detector and a switching unit or an arithmetic unit. The x-ray detector, the network unit and the arithmetic unit can be connected with one another in a distributed system. The communication behavior of the communicating entities is determined by rules and formats.

In the communication various protocols which assume different tasks, for instance Internet protocol family, can be used together. The individual protocols can be organized in layers. Each protocol can belong to a specific layer. Each protocol can be responsible for completing a special task. Protocols of higher layers can use services of protocols of lower layers. The protocols can form a protocol stack in accordance with the ISO-OSI reference model or DoD layer model. Messages from a specific layer are also referred to as protocol data units. The protocol stack may have an application layer according to OSI layer 5 to 7, a transport layer according to OSI layer 4, an Internet or switching layer according to OSI layer 3 and a network access layer according to OSI layer 1 to 2.

The structure of a data packet described in a protocol contains information, which is important to the data exchange, relating to the packet, for instance sender and receiver, the type of packet, the packet size, with multi-part transfers the consecutive number and overall number of packets and a checksum for reproducing an error-free transfer. This information can be prefixed on the useful data as a header or attached as a trailer. The protocol can have an end-to-end control of the transfer. For instance, the transmission control protocol (TCP) as a protocol in the transport layer monitors the complete delivery of the data packets and the data packets are further brought into the correct sequence, so that a cohesive data flow can be submitted to the application. For instance, the User Datagram Protocol (UDP) as a protocol in the transport layer is a protocol with just a minimal overhead, and does not ensure an end-to-end control of the transfer so that datagrams may possibly get lost or the sequential arrangement during receipt does not correspond to that during dispatch.

The tasks of a protocol can comprise a safe and reliable connection set-up between the network components involved in the communication, the reliable delivery of packets, a repeated sending of unarrived packets, a delivery of the data packets to the desired receiver/s, ensuring an error-free transfer, the merging of incoming data packets in the correct sequential arrangement, the prevention of the reading-out by an unauthorized third party and/or the prevention of the manipulation by an unauthorized third party. Protocols which regulate the data traffic in a network can be made available by the network stack to all further programs on the arithmetic unit or the x-ray detector. These protocols can serve as a standard for the data transfer between different systems.

Network-based solutions, for instance Ethernet or TCP/IP, can be used instead of dedicated lines and protocols. Known protocols and implementations for data transfer can advantageously be used. For instance, when the TCP/IP protocol is used, the switching unit can comprise a router. For instance, the switching unit can comprise a switch when Ethernet is used.

According to one embodiment of the invention, an Internet protocol is used for communication between the network unit and the switching unit. TCP, SCTP, TLS or UDP can be used as the Internet protocol for instance. TCP/IP can preferably be used. IP, particularly preferably IPv4 or in particular IPv6 can be used in the Internet or switching layer for instance. MAC or Ethernet can be used in the network access layer for instance. Furthermore, a physical layer can be included in the protocol stack.

Measurement data from the x-detector can be provided directly in the module with a header which identifies the measurement interval and x-ray detector. The data can subsequently be forwarded as TCP/IP packets by way of the network to the arithmetic unit. Since the arithmetic unit can contain TCP/IP functionality, the data can be received and confirmed without extra effort. The development and implementation of special protocols can be advantageously omitted.

According to one embodiment of the invention, the switching unit is connected to a plurality of network units of a plurality of x-ray detectors. The switching unit can be connected to a plurality of network units or x-ray detectors. Each network unit can be included in an individual x-ray detector. Each x-ray detector can comprise an individual network unit. Each switching unit can be assigned a number of network units or x-ray detectors. Advantageously data can be bundled into the switching units or transferred to the arithmetic unit or transfer unit via one or a number of lines. Advantageously the number of connections can be reduced.

According to one embodiment of the invention, the detector apparatus has a plurality of switching units. A tree-like structure can be embodied from arithmetic unit or transfer unit, switching units and x-ray detectors or network units. Advantageously the number of connections can be reduced.

According to one embodiment of the invention, the x-ray detector has a time receiver which is designed to read out data at a predetermined point in time and to send the data with a time stamp. The time receiver can have an accuracy in the region of, in particular a few, microseconds. The time receiver can receive a time signal. The time receiver can synchronize its clock or the clock of the x-ray detector by way of the received time signal with the time signal. A predetermined point in time can be transferred to the time receiver via the connections. The x-ray detector is designed such that it can be read out at the predetermined point in time.

The x-ray detector can be controlled such that it can be read out at the predetermined point in time. For instance, the predetermined point in time can be sent as a data packet to the time receiver or the x-ray receiver. The predetermined point in time can be compared with the synchronized clock of the time receiver or the x-ray detector; the data can be read out when the time coincides with the predetermined point in time.

The data can be provided with a time stamp. The time stamp can correspond to the predetermined point in time for instance. The data can be sent by the x-ray detector via the network unit.

Advantageously a number of or all x-ray detectors can be read out in synchrony or at the same predetermined point in time. Advantageously the data can be assigned to one another on the basis of the time stamp. Brief jitter from the timer can be avoided since clocks run in a stable fashion over a long period of time. The detector apparatus can have at least one x-ray detector, if an external synchronization, with the arithmetic unit across the slip ring for instance, is carried out.

According to one embodiment of the invention, the detector apparatus also has a timer connected to the at least one switching unit, wherein the timer is connected to the time receiver. The detector apparatus can preferably have at least two x-ray detectors, if an internal synchronization is carried out within the detector apparatus.

The timer can be included in the detector apparatus or the arithmetic unit for instance. The timer can preferably be included in the detector apparatus. The timer can be connected to the x-ray detector or the time receiver by way of the switching unit. The timer can have a clock or reference clock. The timer can be designed to synchronize the clocks of the time receivers. The timer can send one or a number of items of time information to the time receivers. The timer can receive one or a number of items of time information from the time receivers. The time receivers can be designed to send information relating to their time to the timer.

The synchronization can be carried out in a one-sided manner or preferably by way of a ping pong method. The timer and the time receiver can send information to one another relating to their time, wherein at least one of the timer and receiver can carry out a comparison of the time of the time receiver with the timer. By way of example, what is known as round trip delay can be used and assessed for comparison purposes for instance.

Network-based protocols, for instance IEEE1588 by way of Ethernet or TCT/IP, can be used instead of dedicated lines and protocols. The network infrastructure available for the data transfer can thus also be used for synchronization. In such cases, in addition to the data of the x-ray detector which is in particular measured or read out, data packets can also have an item of time information. Each x-ray detector can have a clock which can be accurately synchronized with the clocks of the other x-ray detectors and the central reference clock of the timer to a precision of fractions of microseconds. Commands for starting measuring periods are sent in advance with the desired start time, the predetermined point in time, to all x-ray detectors.

Advantageously a number of or all x-ray detectors can be read out at a common predetermined point in time. Commercially available components can advantageously be used for synchronization, e.g. on the basis of IEEE1588, also known as Precision Time Protocol (PTP). Advantageously the network cabling available for the data transfer can be used in addition to the synchronization. The cabling work and the susceptibility to error can advantageously be reduced.

According to one embodiment of the invention, the timer is connected to a plurality of switching units. Advantageously, a number of x-ray detectors, which are connected to the arithmetic unit or the transfer unit by way of at least to some extent different switching units, can be synchronized via the same timer.

At least one embodiment of the invention further relates to a medical device including an embodiment of the detector apparatus, a transfer unit and an arithmetic unit. The arithmetic unit can have a clock or a reference clock for synchronizing the time receiver. The arithmetic unit has at least one network interface, preferably a number of network interfaces. In the arithmetic unit the data can be used to reconstruct two or three-dimensional images.

According to one embodiment of the invention, the medical device is a computed tomography system. A computer program run in the arithmetic unit can assign the angular position during the recording or the reading-out to the data by way of the time stamp and the specification of the x-ray detector, in a header for instance. Advantageously the data can be easily assigned to a recording or a read-out process.

According to one embodiment of the invention, the medical device has a gantry with a stator and a rotor, wherein the detector apparatus is included in the rotor. The detector apparatus forms part of the rotatable rotor. The use of the network protocol takes place within the rotor. The network protocol is used on the connection between the network unit and the switching unit. The network protocol can preferably be used on the connection between the switching unit and the transfer unit. Advantageously a simplified and flexible data transfer can be achieved.

According to one embodiment of the invention, the transfer unit comprises a slip ring transfer system. The slip ring transfer system can comprise a capacitive transfer, a radio transfer or an optical transfer. Advantageously the transfer can be carried out wirelessly.

At least one embodiment of the invention further relates to a method for operating a detector apparatus comprising detecting x-ray radiation via an x-ray detector and in the process detecting data, and of transferring data from the network unit to the switching unit via a network protocol. The detection can comprise reading out data. Advantageously the integration of the network into the detector apparatus or the communication link toward the switching unit, transfer unit or arithmetic unit can be simplified or made quicker. Advantageously in troubleshooting available data network tools can be accessed.

According to one embodiment of the invention, the method further includes synchronizing a plurality of time receivers. The synchronizing can comprise an internal synchronization within the detector apparatus or an external synchronization, for instance with the arithmetic unit. The timer can have a reference clock.

The timer can be designed to synchronize the clocks of the time receivers. The timer can send one or a number of items of time information to the time receivers. The timer can receive one or a number of items of time information from the time receivers. The time receivers can be designed to send information relating to their time to the timer.

The synchronization can be carried out in a one-sided manner or preferably by way of a ping pong method. The timer and the time receiver can send information to one another relating to their time, wherein at least one of the timer and receiver can carry out a comparison of the time of the time receiver with the timer. By way of example, what is known as round trip delay can be used and assessed for comparison purposes for instance.

Network-based protocols, for instance IEEE1588, also known as Precision Time Protocol (PTP) can be used by way of Ethernet or TCT/IP instead of dedicated lines and protocols. The Precision Time Protocol is a network protocol which can cause the synchronicity of the clock settings of several devices in a computer network.

The network infrastructure available for the data transfer can thus also be used for synchronization. In such cases, data packets, in addition to the data of the x-ray detector which is in particular measured or read out, can also have an item of time information. Each x-ray detector can have a clock which can be accurately synchronized with the clocks of the other x-ray detectors and the central reference clock of the timer to a precision of fractions of microseconds.

A PTP network consists of communicating clocks. The PTP network has a reference clock. The PTP network can have a typical clock which is either the time receiver or the timer, but not both. Simple clocks synchronize directly. The PTP network can have what is known as a boundary clock which transports the time information past a network boundary. The PTP network can have what is known as a transparent clock (TC), which improves the forwarding of time information within a network by it receiving and correctly forwarding the PTP messages.

During operation, in each case the reference clock or the timer distributes the time signal to the time receivers in order to determine what is known as the time delay. To this end, a time marker in the form of a sync message is conveyed by the reference clock to the time receiver which determines the receive time of the time markers at its distinct time. Moreover, the time receiver repeatedly sends a delay request message to the timer, the receive time of which at the timer is in turn sent back as a delay response message to the time receiver.

The master-to-slave delay between the timer and time receiver and the slave-to-master delay between the time receiver and timer are determined from the differences between the four time markers in each case. These values contain the difference between the two clocks and message delay time with opposite signs. The average value of the two variables thus supplies the directional offset to the timer, which can finally be used to synchronize the clock of the time receiver. Alternatively, what is known as the round trip delay can be determined.

The compensation of the delay times can be supported here by the assumption that forward and return path of synchronization messages have the same average delay times and only slowly change with the time. The time receiver can approach the reference time of the timer continuously by way of a control method. In particular, returns in the time of the time receiver can thus be avoided.

Commercially available components can advantageously be used for synchronization, e.g. on the basis of IEEE1588, also known as Precision Time Protocol (PTP). Advantageously the network cabling available for the data transfer can be used in addition to the synchronization. The cabling work and the susceptibility to error can advantageously be reduced.

According to one embodiment of the invention, the data is detected at a predetermined point in time. Commands for starting measuring periods or the reading-out are sent in advance with the desired start time, the predetermined point in time, to all x-ray detectors. Advantageously a number of or all x-ray detectors can be read out at a common predetermined point in time.

According to one embodiment of the invention, the data has a time stamp. In the detection step a time stamp can be assigned to the data. A computer program executed in the arithmetic unit can assign the data of a read-out process to one another by way of the time stamp and the specification of the x-ray detector, for instance in a header. Advantageously the data of a recording or of a read-out process can be easily assigned with the aid of the time stamp.

FIG. 1 shows an example embodiment of the inventive computed tomography system 31 according to a first embodiment having an inventive detector apparatus 29 according to a first embodiment. The computed tomography system 31 has a detector apparatus 29. The computer tomograph 29 further has an arithmetic unit 45. A transfer unit 34, for instance a slip ring transmission system, is embodied for data transfer between the detector apparatus 29 and the arithmetic unit 45. The transfer unit 34 is connected to the arithmetic unit 45 by way of connections 19. The detector apparatus 29 has three switching units 11 by way of example. The switching units 11 are connected to the transfer unit 34 by way of connections 17.

Network units 3 of a number of x-ray detectors 1 are connected to each switching unit 11 by way of connections 7. The x-ray detectors 1 each have a network unit 3. The connections 7, 17, 19 can be embodied for instance only for communication in one direction toward the arithmetic unit. The connections 17, 19 are embodied as a 10 GBit Ethernet connection or an optical connection. The connections 7 are embodied as a 1 GBit Ethernet connection. The data transfer over the connections 7, 17, 19 is based on network protocols or Internet protocols, for instance TCP/IP with IPv4 and Ethernet.

Figure 2:
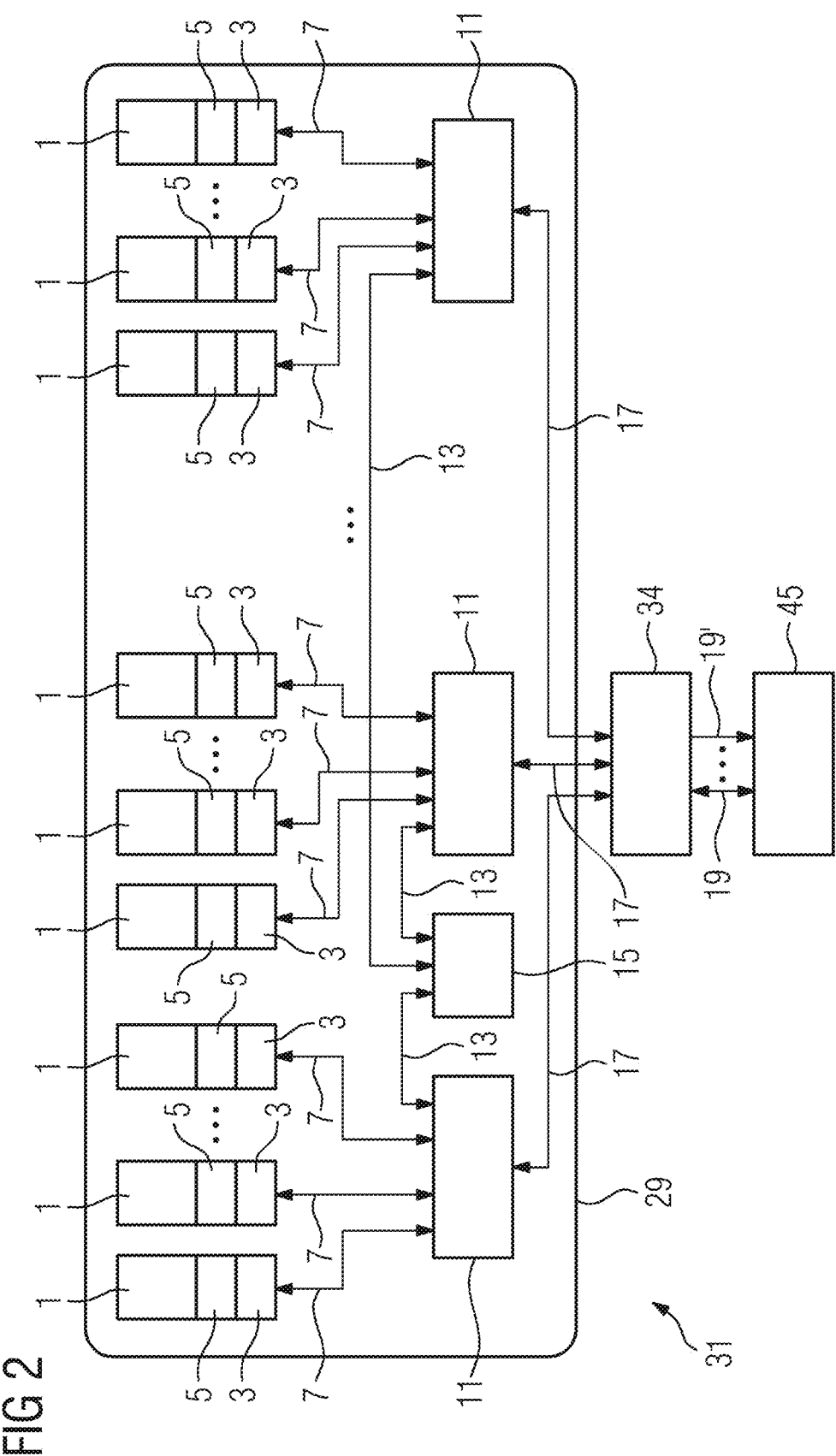
FIG. 2 shows a schematic representation of a concept of an inventive computed tomography system according to a second embodiment having an inventive detector apparatus according to a second embodiment.

FIG. 2 shows an example embodiment of the inventive computed tomography system 31 according to a second embodiment having an inventive detector apparatus 29 according to a second embodiment. The x-ray detectors 1 further have a time receiver 5. The detector apparatus further has a timer 15, which is connected to the switching unit 11 by way of connections 13. The connections 7, 13, 17, 19 can be embodied for instance for communication in both directions simultaneously or alternately. In addition, a connection 19' can be embodied for communication in just one direction, in particular toward the arithmetic unit. The connections 17, 19, 19' are embodied as a 10 GBit Ethernet connection or an optical connection. The connections 7, 13 are embodied as a 1 GBit Ethernet connection. The synchronization of the time receiver 5 in connection with the timer 15 is based on IEEE1588, also known as Precision Time Protocol (PTP).

Figure 3:
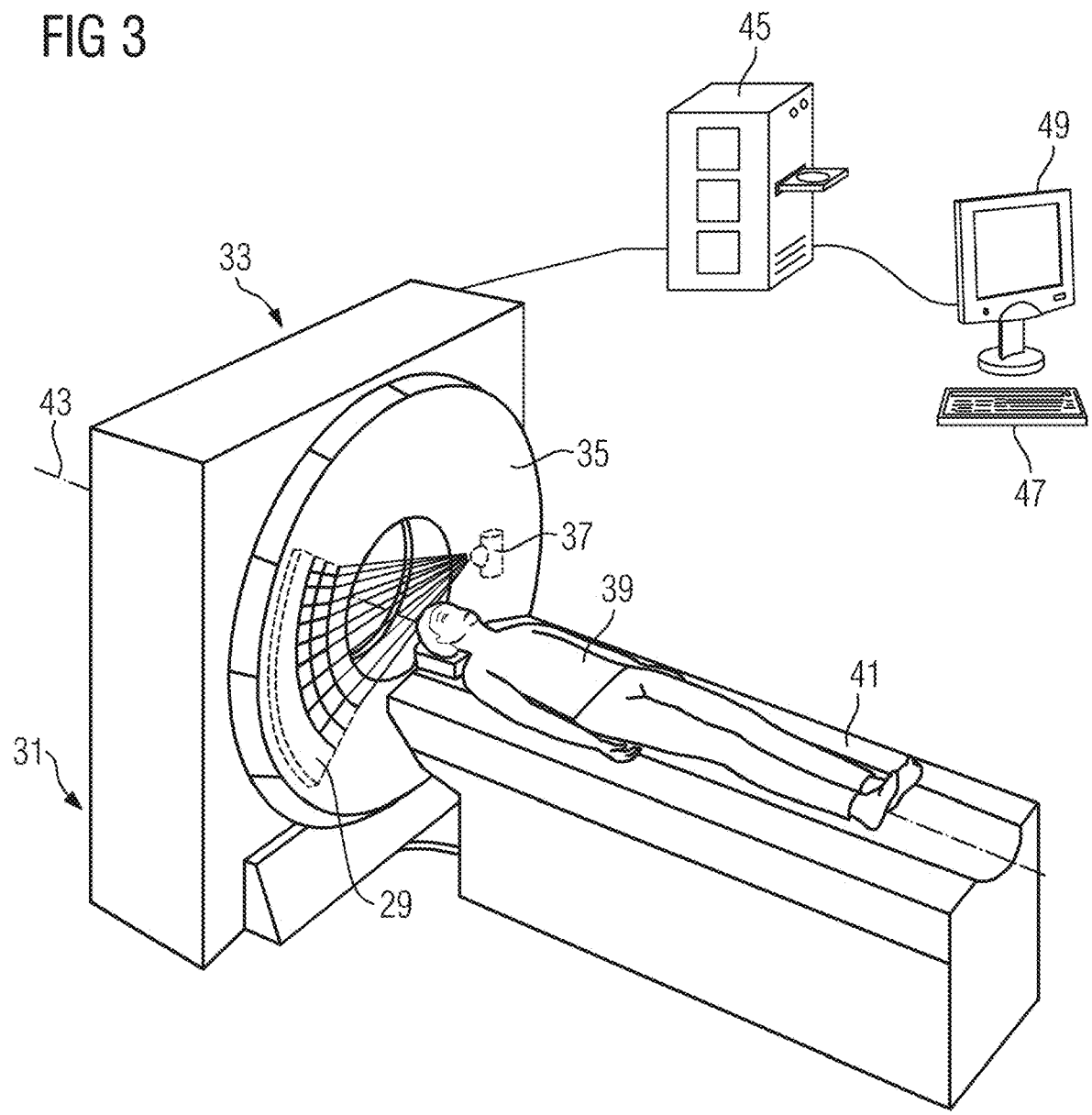
FIG. 3 shows a schematic representation of a concept of an inventive computed tomography system according to a third embodiment.

FIG. 3 shows an example embodiment of the inventive computed tomography system 31 according to a third embodiment. The computed tomography system 31 contains a gantry 33 with a rotor 35. The rotor 35 comprises an x-ray source 37 and the detector apparatus 29. The detector apparatus 29 forms part of the rotatable rotor 35. The network protocol is used within the rotor 35. The network protocol is used on the connection 7 between the network unit 3 and the switching unit 11. The network protocol is used on the connection 17 between the switching unit 11 and the transfer unit 34. A transfer unit 34, for instance a slip ring transmission system, is embodied for data transfer between the detector apparatus 29 and the arithmetic unit 45. The examination object 39 is supported on the patient couch 41 and can be moved along the axis of rotation z 43 through the gantry 33. An arithmetic unit 45 is used to control and calculate the sectional images and to carry out the inventive method. An input facility 47 and an output apparatus 49 are connected to the arithmetic unit 45.

Figure 4:
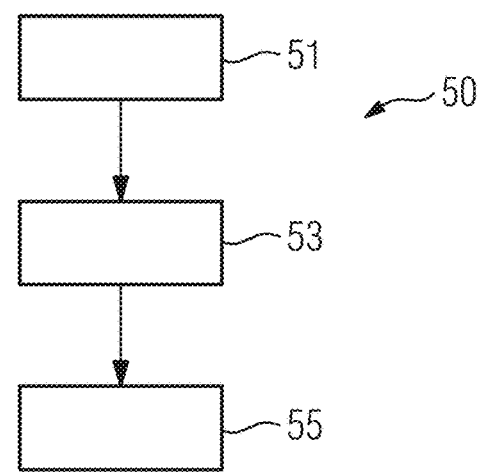
FIG. 4 shows a schematic representation of a concept of an embodiment of an inventive method.

FIG. 4 shows an example embodiment of the inventive method 50 for operating a detector apparatus. The method 50 has the steps of synchronizing 51, detecting 53 and transferring 55. The step of synchronizing 51 can comprise an internal synchronization within the detector apparatus or an external synchronization, for instance with the arithmetic unit. The timer can have a reference clock. The timer is designed to synchronize the clocks of the time receivers. The timer sends one or a number of items of time information to the time receivers. The timer receives one or a number of items of time information from the time receivers. The time receivers are designed to send information relating to their time to the timer. The synchronization is carried out by way of a ping pong method, for instance using the PTP protocol. The timer and the time receiver send information to one another relating to their time, wherein at least one of the timer and receiver can carry out a comparison of the time of the time receiver with the timer. By way of example, what is known as round trip delay can be used and assessed for comparison purposes for instance. In the detection step 53, x-ray radiation is detected via an x-ray detector and data is acquired or read out in the process. The acquisition of data can comprise a step of reading out data. In the transfer step 55, data is transmitted to the arithmetic unit via a network protocol, preferably via an Internet protocol, for instance TCP/IP.

Although the invention has been disclosed in detail with the preferred example embodiment, the invention is not restricted by the examples given and other variations can be derived therefrom by a person skilled in the art without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector apparatus for use as part of a data network, comprising:
    a plurality of x-ray detectors, each of the plurality of x-ray detectors including a network-capable network interface; and
    a switch or router, connected to each of the network-capable network interfaces of the plurality of x-ray detectors, each of the plurality of x-ray detectors including a distinct IP address such that the data network is adjustable to take a change in a number of the plurality of x-ray detectors into account,
    wherein the plurality of x-ray detectors are configured to detect x-rays generated from a single x-ray source.

2. The detector apparatus of claim 1, wherein the network-capable network interfaces are configured to transfer data via an Internet protocol.

3. The detector apparatus of claim 1, wherein the network-capable network interfaces and the switch or router are configured to communicate with each other over a network protocol.

4. The detector apparatus of claim 1, wherein the network-capable network interfaces and the switch or router are configured to transfer data via an Internet protocol.

5. The detector apparatus of claim 1, wherein the switch or router includes a plurality of switches or routers and wherein the detector apparatus includes the plurality of switches or routers, and each of the plurality of switches or routers are connected to the network-capable network interface of at least one of the plurality of x-ray detectors.

6. The detector apparatus of claim 1, further comprising:
    a timer connected to the switch or router.

7. The detector apparatus of claim 6, wherein the switch or router includes a plurality of switches or routers and wherein the timer is connected to the plurality of switches or routers.

8. The detector apparatus of claim 1, wherein each of the plurality of x-ray detectors includes a time receiver, and a same point in time is synchronizable to a clock of each of the time receivers to enable a data to be read out when a time coincides with the same point in time.

9. The detector apparatus of claim 1, wherein the switch or router includes a plurality of switches or routers and wherein a timer is connected to the plurality of switches or routers.

10. A medical device having:
    the detector apparatus of claim 1;
    a transfer unit; and
    an arithmetic unit.

11. The detector apparatus of claim 1, wherein,
    the switch or router includes a plurality of switches or routers, and
    the detector apparatus further comprises a timer connected to the plurality of switches or routers.

12. A rotor for a medical device comprising:
    an x-ray source; and
    a detector apparatus configured to detect x-rays generated from the x-ray source, wherein the detector apparatus includes,
    a plurality of x-ray detectors, each of the plurality of x-ray detectors including a network-capable network interface, and
    a switch or router, connected to each of the network-capable network interfaces of the plurality of x-ray detectors, each of the plurality of x-ray detectors including a distinct IP address such that a data network associated with the detector apparatus is adjustable to take a change in a number of the plurality of x-ray detectors into account.

13. A medical device comprising:
    the rotor of claim 12, wherein the medical device includes a computed tomography system.

14. A medical imaging device comprising:
    the rotor of claim 12; and
    a stator.

15. The medical imaging device of claim 14, further comprising:
    a patient couch configured to move into and out of the rotor.

16. The medical imaging device of claim 14, wherein the data network further includes an arithmetic unit.

17. The rotor of claim 12, wherein the x-ray source is on one side of the rotor, and at least one of the plurality of x-ray detectors is on an opposite side of the rotor.

18. The rotor of claim 12, wherein the network-capable network interfaces are configured to transfer data via a network protocol, and
    the network protocol is used within the rotor.

19. A method for operating an apparatus of a data network, the method comprising:
    detecting x-ray radiation via a plurality of x-ray detectors, the x-ray radiation generated from a single x-ray source, each of the plurality of x-ray detectors including a network-capable network interface;

acquiring data from the network-capable interfaces; and
transferring the data acquired from the network-capable network interfaces of the plurality of x-ray detectors to a switch or router, via a network protocol, each of the plurality of x-ray detectors including a distinct IP address such that the data network is adjustable to take a change in a number of the plurality of x-ray detectors into account.

20. The method of claim 19, wherein the data includes a time stamp.

* * * * *